United States Patent
Galambos et al.

(10) Patent No.: US 6,537,437 B1
(45) Date of Patent: Mar. 25, 2003

(54) SURFACE-MICROMACHINED MICROFLUIDIC DEVICES

(75) Inventors: Paul C. Galambos, Albuquerque, NM (US); Murat Okandan, Albuquerque, NM (US); Stephen Montague, Albuquerque, NM (US); James H. Smith, Redmond, WA (US); Phillip H. Paul, Livermore, CA (US); Thomas W. Krygowski, Cortlandt Manor, NY (US); James J. Allen, Albuquerque, NM (US); Christopher A. Nichols, Hauppauge, NY (US); Jerome F. Jakubczak, II, Rio Rancho, NM (US)

(73) Assignee: Sandia Corporation, Albuquerque, NM (US)

( * ) Notice: Subject to any disclaimer, the term of this patent is extended or adjusted under 35 U.S.C. 154(b) by 143 days.

(21) Appl. No.: 09/712,634

(22) Filed: Nov. 13, 2000

(51) Int. Cl.$^7$ ................................................. G01N 27/26
(52) U.S. Cl. ........................ 204/600; 204/601; 204/606; 204/660
(58) Field of Search ................................ 204/600, 601, 204/606, 660

(56) References Cited

U.S. PATENT DOCUMENTS

| | | | |
|---|---|---|---|
| 5,501,893 A | 3/1996 | Laermer | 428/161 |
| 5,582,701 A * | 12/1996 | Geis et al. | 204/451 |
| 5,591,139 A | 1/1997 | Lin | 604/264 |
| 5,804,084 A | 9/1998 | Nasby | 216/2 |
| 5,824,204 A * | 10/1998 | Jerman | 204/601 |
| 5,985,119 A | 11/1999 | Zanzucchi | 204/450 |
| 6,013,164 A | 1/2000 | Paul | 204/450 |
| 6,033,544 A | 3/2000 | Demers | 204/450 |
| 6,096,656 A | 8/2000 | Matzke | 438/702 |

OTHER PUBLICATIONS

L. Bousse and S. Mostarshed, "The Zeta Potential of Silicon Nitride," *Journal of Electroanalytical Chemistry*, vol. 302, pp. 269–274 (1991).

P.H. Paul, D.W. Arnold and D.J.Rakestraw, "Electrokinetic Generation of High Pressures Using Porous Microstructures," *Proceedings of Micro Total Analysis Systems (μTAS)* '98, pp. 49–52 (Oct. 1998).

P. Galambos, B. Eaton, J. Smith, R. Shul, C.W. Gober, J. Sniegowski, S. Miller and D. Guttierez, "Surface Micromachined Microfluidics: Design, Fabrication, Packaging, and Characterization," Paper presented at the 1999 International Mechanical Engineering Congress and Exposition, Nashville, TN, Nov. 14–19, 1999.

A.V. Lemoff and A.P. Lee, "An AC Magnetohydrodynamic Micropump," *Sensors and Actuators B*, vol. 63, pp. 178–185 (2000).

* cited by examiner

Primary Examiner—Arun S. Phasge
(74) Attorney, Agent, or Firm—John P. Hohimer

(57) ABSTRACT

Microfluidic devices are disclosed which can be manufactured using surface-micromachining. These devices utilize an electroosmotic force or an electromagnetic field to generate a flow of a fluid in a microchannel that is lined, at least in part, with silicon nitride. Additional electrodes can be provided within or about the microchannel for separating particular constituents in the fluid during the flow based on charge state or magnetic moment. The fluid can also be pressurized in the channel. The present invention has many different applications including electrokinetic pumping, chemical and biochemical analysis (e.g. based on electrophoresis or chromatography), conducting chemical reactions on a microscopic scale, and forming hydraulic actuators.

53 Claims, 12 Drawing Sheets

Section 1 - 1

Section 2 - 2

Section 3 - 3

Section 4 - 4

Section 5 - 5

Section 6 - 6

Section 7-7

1

SURFACE-MICROMACHINED MICROFLUIDIC DEVICES

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates to microfluidic devices fabricated by surface micromachining, and in particular to electrokinetic pumps and hydraulic actuators formed on a substrate by surface micromachining.

BACKGROUND OF THE INVENTION

Surface micromachining utilizes conventional integrated circuit (IC) processing steps to form mechanical or electromechanical devices on a substrate (typically silicon) by building up a structure for a particular device layer by layer. Although many different types of electrostatic actuators can be formed by surface micromachining, the force which can be produced by electrostatic actuators is generally limited. Furthermore, electrostatic actuators are generally limited to motion in the plane of the substrate.

Microfluidic devices based on electrokinetic pumping are capable of producing very high hydraulic pressures of up to 2500 psi without any moving parts (see, e.g. U.S. Pat. Nos. 6,013,164 and 6,019,882 to Paul et al). Such electrokinetic microfluidic devices, based on an electroosmotic flow of a fluid through a microchannel produced by an applied electric potential, necessarily require that there be a porous dielectric medium present in the microchannel.

The present invention is a surface-micromachined microfluidic apparatus formed on a substrate using surface-micromachining, with many applications including pumping or pressurizing a fluid, separating different constituents in a fluid, conducting chemical reactions on a micro-scale, and forming hydraulic actuators.

An advantage of the present invention is that surface micromachining processes can be used to form one or more microfluidic devices in a monolithic form on a substrate.

Another advantage of the present invention is that the microfluidic device can be electrically isolated from the substrate to allow a plurality of electrical connections to be made to the microfluidic device, to allow a plurality of microfluidic devices to be formed on the same substrate, or to allow fabrication on an electrically conducting substrate.

Yet another advantage is that, in some preferred embodiments of the present invention, an electroosmotic force can be produced to act upon a fluid without the need for a microporous dielectric medium as has been heretofore required.

Still another advantage of the present invention is that a series of surface micromachining process steps can be used to form an electroosmotic microfluidic devices, an electromagnetic microfluidic device or a combination thereof on the same substrate.

These and other advantages of the present invention will become evident to those skilled in the art.

SUMMARY OF THE INVENTION

The present invention relates to a surface-micromachined apparatus, comprising a microchannel (also termed herein a microfluidic channel, a fluid-flow channel or simply a channel) formed on a substrate (e.g. comprising silicon) from a plurality of deposited and patterned layers of polycrystalline silicon (also termed polysilicon) and silicon nitride, with the silicon nitride at least partially lining the microchannel, and means for generating an electroosmotic force or electromagnetic field in the microchannel.

In some embodiments of the present invention, the microchannel can include a constricted portion having a lateral dimension smaller than the lateral dimension of the remainder of the microchannel. For example, the constricted portion can have a height that is smaller than the height of the remainder of the microchannel, with the height of the constricted portion generally being in the range of 0.1–1 microns. An overall width of the constricted portion of the microchannel can be in the range of 0.05–10 millimeters depending upon a particular application. The exact shape of the microchannel and the constricted portion thereof is defined by a removable sacrificial material such as silicon dioxide or a silicate glass. The silicon nitride, which at least partially lines the microchannel, can have a thickness, for example, in the range of 0.1–2 microns.

In other embodiments of the present invention, the microchannel can include a plurality of spaced posts extending outward from at least one wall thereof to increase the surface area in the channel, with the posts being lined with the silicon nitride. These spaced posts can be used in embodiments of the present invention wherein the microchannel is unconstricted, or in embodiments wherein the microchannel includes a constricted portion thereof.

The means for generating the electroosmotic force or electromagnetic field in the microchannel in one embodiment of the present invention comprises a plurality of electrodes for generating an electric potential within the microchannel in response to a voltage provided to the electrodes, with the voltage generally being limited to about 1000 volts or less. The electrodes can be formed from any electrically-conductive material such as polycrystalline silicon, a metal or metal alloy, and carbon (e.g. a doped deposited diamond-like form of carbon).

Various configurations of the electrodes are possible. To generate an electroosmotic force, a first electrode can be located proximate to one end of the constricted portion of the microchannel, and a second electrode can be located proximate to the other end of the constricted portion of the microchannel so that an electric field is produced along the length of the constricted portion to produce a force which acts upon a fluid within the constricted portion. One or more additional electrodes can be located in or proximate to the microchannel between the first and second electrodes to aid in generating the electroosmotic force or to effect an electric field separation of constituent components in the fluid. These additional electrodes can be spaced across the width of the constricted portion of the microchannel, along the length of the constricted portion, above and below the constricted portion, or a combination thereof.

The means for generating the electroosmotic force or electromagnetic field in the microchannel in another embodiment of the present invention comprises a coil formed about a portion of the microchannel. The coil, which can have a rectangular cross-section shape with a height that is generally smaller than a width thereof, can be activated by an electrical current to produce the electromagnetic field in the microchannel.

In each of the above embodiments of the present invention, a fluid (e.g. an electrolyte) can be introduced into the microchannel at an entrance port at one end of the microchannel. The fluid is moveable within the microchannel in response to the generated electroosmotic force or the electromagnetic field. In this way, the fluid can be conveyed through the microchannel from the entrance port thereof to an exit port thereof. One or more of the entrance and exit ports can be formed to extend through the thickness of the substrate to a back side thereof where fluidic connections can be made to the substrate.

In some embodiments of the present invention, the fluid flow can be blocked at one end of the microchannel, for example, to form a hydraulic actuator comprising a closed chamber connected to the microchannel, with the chamber having one or more walls thereof that are moveable in response to a change in pressure of the fluid. In this case, the electroosmotic force or electromagnetic field can be used to pressurize the fluid and displace each moveable wall of the chamber. An actuator arm, lever, linkage, compliant mechanism or a combination thereof can be used to transmit the motion of the moveable wall to a load which can be located either in the plane of the substrate or at an angle (e.g. 90°) to the substrate. In this way, a hydraulic actuator can be formed to provide an actuator force much larger than the force which is possible with a conventional electrostatic actuator.

The present invention also relates to a surface-micromachined apparatus, comprising a microfluidic channel formed on a substrate and defined, at least in part, by a first layer of silicon nitride, and a second layer of silicon nitride overlying the first layer, with the second silicon nitride layer being nonplanar and thereby forming a constricted portion of the channel having a height that is smaller than the height of the remainder of the channel, and means, located within the channel, for generating a flow of a fluid in the channel. The channel can be further defined by at least one layer of polycrystalline silicon overlying the second layer of silicon nitride. When a pair of polycrystalline silicon layers are provided overlying the second silicon nitride layer, the two layers of the polycrystalline silicon can be separated by a third layer of silicon nitride.

The flow generating means can comprise a first plurality of electrodes disposed in the channel, with the first plurality of electrodes being spaced about the length of the channel to generate an electroosmotic force on the fluid in response to a voltage applied between at least two of the first plurality of electrodes. In some embodiments of the present invention, a second plurality of electrodes can also be provided in the channel or proximate thereto and spaced across a lateral dimension of the channel to alter the flow of the fluid in the channel (e.g. through an electric field which acts upon different constituents of the fluid differently to separate the constituents in space or time or both).

The first plurality of electrodes are generally substantially planar and oriented in a direction substantially perpendicular to the substrate. The second plurality of electrodes are also generally substantially planar and can be oriented either in a direction substantially perpendicular to the substrate, or in a direction substantially coplanar with the substrate, or both.

Electrical wiring can be formed on the substrate below the first layer of silicon nitride or above the second layer of silicon nitride and connected to the first plurality of electrodes to provide the voltage thereto. Similar wiring can be used to provide electrical connections to the second plurality of electrodes.

As described previously, an entrance port can be provided on one side of the constricted portion of the channel, and an exit port can be provided on the other side of the constricted portion. One or both of the entrance and exit ports can extend through the thickness of the substrate to a back side thereof.

In some embodiments of the present invention, the flow generating means can comprise a coil formed about the channel to produce an electroosmotic field in response to an electrical current flowing through the coil. The coil can be formed from a plurality of turns of an electrical conductor, with each turn further comprising a first portion of the electrical conductor underlying the first layer of silicon nitride, and a second portion of the electrical conductor overlying the second layer of silicon nitride. Electrical wiring can be formed on the substrate below the first layer of silicon nitride or above the second layer of silicon nitride and connected to the coil to provide the electrical current.

To form a hydraulic actuator, a chamber having a deformable or moveable wall can be provided in communication with one end of the channel, with the wall being deformable or moveable in response to a change the flow of the fluid in the channel. The deformable or moveable wall can then be connected to a load using an actuator arm, lever, linkage, compliant mechanism or a combination thereof.

The present invention is further related to a surface-micromachined apparatus, comprising a fluid-flow channel formed on a silicon substrate and lined, at least in part, with silicon nitride; a plurality of vertically-disposed electrical conductors spaced along a portion of the length of the channel either inside or outside of the channel, with the vertically-disposed electrical conductors being oriented substantially perpendicular to the substrate; and electrical wiring formed underneath the channel for electrical activation of the vertically-disposed electrical conductors.

When the vertically-disposed electrical conductors are located inside the channel, these conductors can be electrically activated to produce an electroosmotic force on a fluid within the channel, thereby moving or pressurizing the fluid. To aid in generating the electroosmotic force, a portion of the channel can be constricted with a lateral dimension smaller than the lateral dimension of the remainder of the channel.

When the vertically-disposed electrical conductors are located outside the channel, a plurality of horizontally-disposed electrical conductors can also be provided oriented substantially parallel to the substrate, with each horizontally-disposed electrical conductor being electrically connected to a pair of the vertically-disposed electrical conductors, thereby forming a coil about the channel. Upon electrical activation, the coil produces an electromagnetic field which can act upon a fluid within the channel, thereby moving or pressurizing the fluid or separating particular constituents therein.

Additionally, the present invention relates to a method for forming a fluid-flow channel on a substrate, comprising steps for depositing a first layer of silicon nitride on the substrate; depositing at least one layer of a sacrificial material (e.g. silicon dioxide or a silicate glass) over the first layer of silicon nitride, and patterning the sacrificial material to define a nonuniform shape for the channel, with the nonuniform shape including a constricted portion of the channel which has a height that is smaller than the height of the remainder of the channel; depositing a second layer of silicon nitride over the patterned sacrificial material, with the second layer of silicon nitride conforming to the nonuniform shape of the channel; forming a plurality of vertically-disposed electrical conductors spaced along the length of the constricted portion; and removing the sacrificial material from the channel.

A further step can be provided for forming a plurality of horizontally-disposed electrical conductors, with each horizontally-disposed electrical conductor being electrically connected to a pair of the vertically-disposed electrical conductors, thereby forming a coil.

Another step can be provided for forming electrical wiring below the first layer of silicon nitride, with the electrical wiring being electrically connected to the plurality of vertically-disposed electrical conductors for activation thereof.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1A:
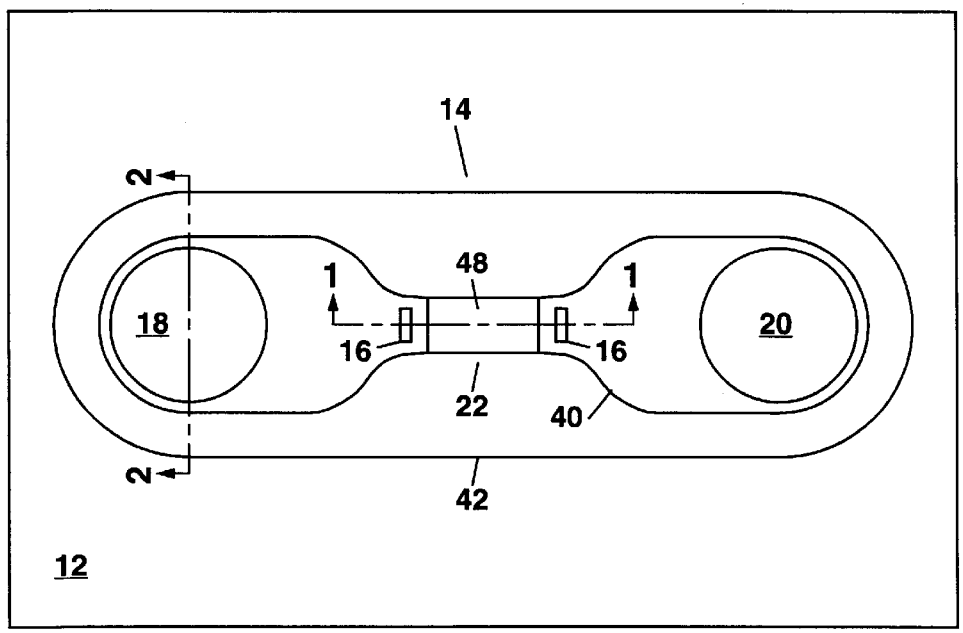
FIG. 1A shows a schematic plan view of a first embodiment of the present invention.
Figure 1B:
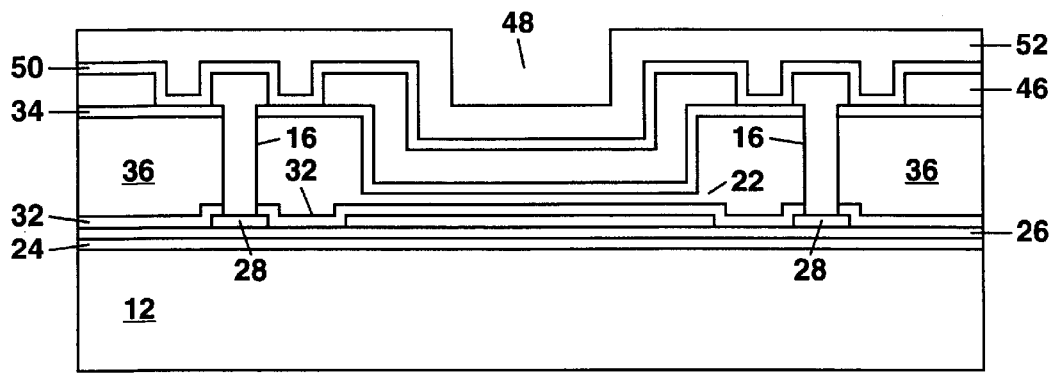
FIGS. 1B and 1C show schematic cross-section views of the device of FIG. 1A along the section lines 1—1 and 2—2, respectively.
Figure 1C:
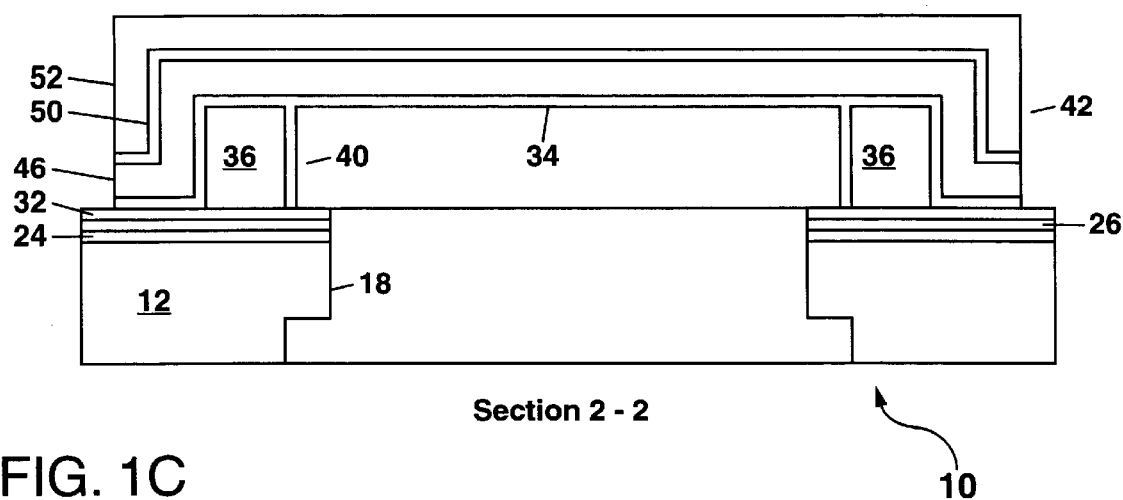

Referring to FIGS. 1A–1C, there is shown a first embodiment of the surface-micromachined apparatus 10 of the present invention. The surface-micromachined apparatus 10 is formed on a substrate 12 and comprises a microchannel 14 (hereinafter channel) formed from a plurality of deposited and patterned layers of polycrystalline silicon (hereinafter polysilicon) and silicon nitride, with the silicon nitride at least partially lining the channel 14. A pair of vertically-disposed electrodes 16 is provided in the channel 14 for generating an electric potential therein, with the electric potential further producing an electric field that acts upon a fluid introduced into the channel 14 through an entrance port 18 to move the fluid through the channel 14 and into an exit port 20 by the force of electroosmosis. Electroosmosis as used herein refers to a process which utilizes an electric potential applied to an electrolyte (i.e. a fluid containing ions and generally capable of ionic conduction) in contact with a dielectric surface (e.g. silicon nitride) to produce a net force on the fluid and thereby produce a net flow of the fluid down the channel 14. Such fluidic motion produced by electroosmosis is also referred to herein as electrokinetic pumping, and a device which performs electrokinetic pumping is referred to herein as an electrokinetic pump.

To aid in generating the electroosmotic force, a portion 22 of the channel 14 in FIG. 1A can be constricted to provide at least one lateral dimension that is smaller than a corresponding lateral dimension of the remainder of the channel 14. In the schematic cross-section view of FIG. 1B, the height of the channel 14 is reduced at the constricted portion 22 to be, for example, 0.1 micron ($\mu$m) while the remainder of the channel 14 has a height of, for example, 2–3 $\mu$m (see FIG. 1C).

In FIG. 1A, the width of the channel 14 can also be reduced at the constricted portion 22 and can be, for example, 50 $\mu$m. Depending upon a particular application and a desired flow rate or pressure generation, the lateral dimensions of the channel 14 and constricted portion 22 can be selected so that the height is in the range of 0.1–1 $\mu$m and the width is in the range of 0.05–10 millimeters (mm). When the width of the constricted portion 22 is relatively large (e.g. $\geq$0.1 mm), a plurality of longitudinal ribs (not shown) can be provided spaced across the width of the constricted portion and extending from the roof to the floor of the constricted portion and aligned along a direction of fluid flow in the channel 14. This forms a segmented flow channel 14 and helps to maintain the height of the constricted portion 22 with changes in pressure therein. It also increases the surface area in the channel 14 for more effective electrokinetic pumping. Lining the constricted portion 22 with an electrically insulating layer of silicon nitride is also important in generating the electroosmotic force since other materials (e.g. polysilicon) forming the channel 14 can be electrically conductive.

Fabrication of the apparatus 10 of FIGS. 1A and 1B will now be described with reference to FIGS. 2A–2I which illustrate a series of surface-micromachining process steps which can be used to build up the apparatus 10 layer by layer. While only a single device 10 is shown in the cross-section views of FIGS. 2A–2I, it will be understood that many devices 10 can be fabricated simultaneously on a single wafer 12 with the same or different construction.

In FIGS. 2A–2I, only selected process steps are illustrated as needed to understand the present invention. Those skilled in the art will understand that surface micromachining involves the deposition and patterning of a plurality of material layers. The term "patterning" as used herein refers to a sequence of well-known integrated circuit (IC) processing steps including applying a photoresist to the substrate 12, prebaking the photoresist, aligning the substrate 12 to a photomask (also termed a reticle), exposing the photoresist through the photomask, developing the photoresist, baking the wafer, etching away the surfaces not protected by the photoresist, and stripping the protected areas of the photoresist so that further processing can take place. The term "patterning" can further include the formation of a hard mask (e.g. comprising about 500 nanometers of a silicate glass deposited from the decomposition of tetraethylortho silicate, also termed TEOS, by low-pressure chemical vapor deposition at about 750° C. and densified by a high temperature processing) overlying a polysilicon or sacrificial material layer in preparation for defining features into the layer by etching.

Figure 2A:
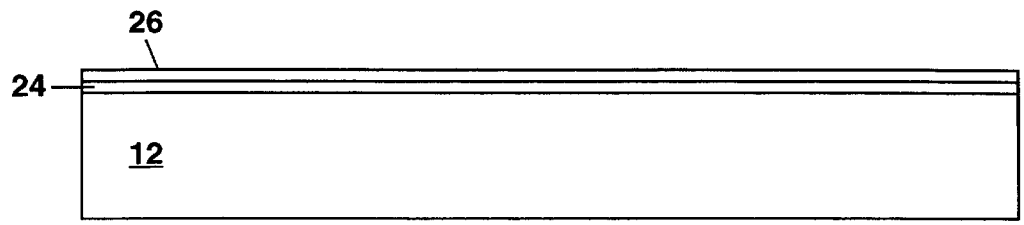
FIGS. 2A–2I schematically illustrate formation of the first embodiment of the present invention using a series of surface-micromachining process steps.

In FIG. 2A, a substrate 12 is provided to begin the process of fabricating the surface-micromachined apparatus 10 of the present invention. The substrate will generally comprise silicon (e.g. a silicon or silicon-on-oxide wafer or portion thereof) although other types of substrates 12 can be used (e.g. comprising glass, quartz, fused silica, ceramic, metal). The substrate can be electrically conducting or electrically insulating since electrical connections to the apparatus 10 are made to portions thereof which are electrically isolated from the substrate 12.

The substrate 12 can be initially prepared by forming a layer of thermal oxide 24 (e.g. about 0.6 $\mu$m thick) on exposed surfaces of the substrate 12. This can be done using a conventional wet oxidation process at an elevated temperature (e.g. 1050° C. for about 1.5 hours). A layer of low-stress silicon nitride 26 (e.g. 0.8 $\mu$m thick) can then be deposited over the thermal oxide layer using low-pressure chemical vapor deposition (LPCVD) at about 850° C. LPCVD is a conformal deposition process which deposits the silicon nitride or other deposited material conformally over exposed surfaces of the substrate 12. The thermal oxide and silicon nitride layers, 24 and 26, provide electrical isolation from the substrate 12 for a subsequently-deposited first polysilicon layer (hereafter Poly-0) which can be patterned to form wiring for making electrical connections to the electrodes 16.

Figure 2B:
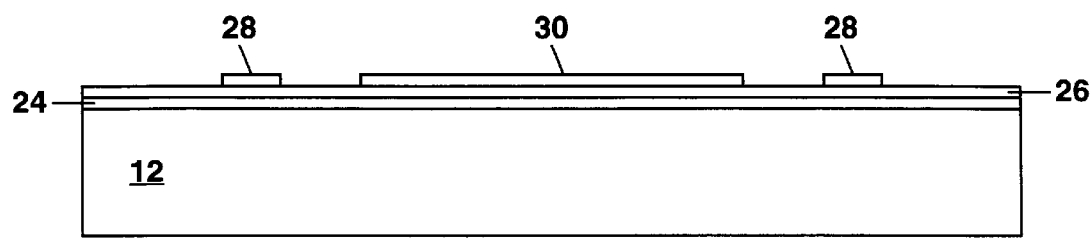
Figure 3A:
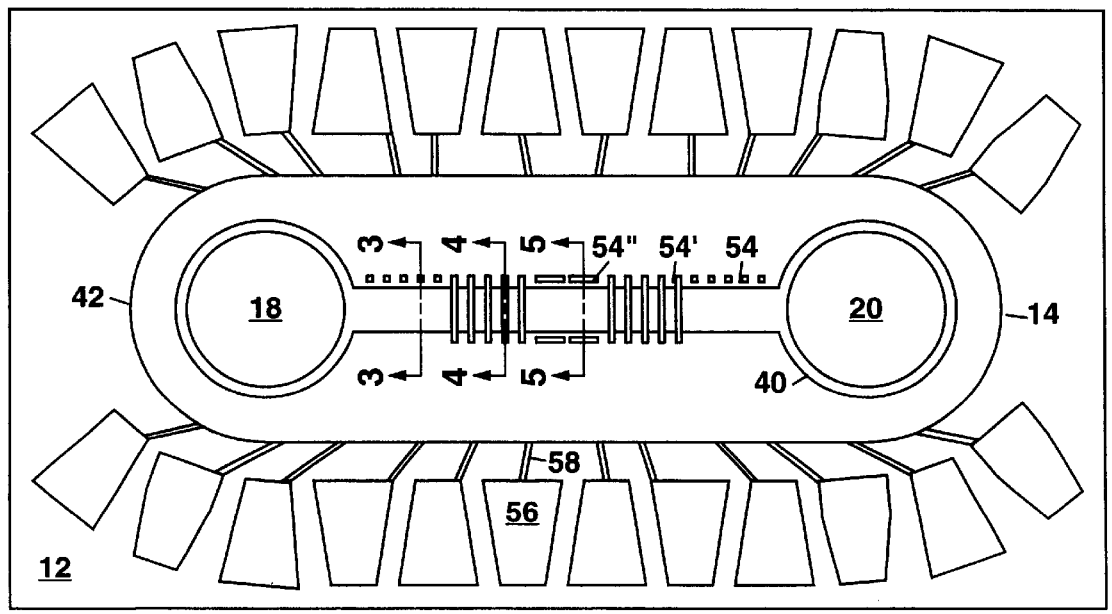
FIG. 3A shows a schematic plan view of a second embodiment of the present invention.

In FIG. 2B, the Poly-0 layer is deposited over the substrate 12 and thermal oxide and silicon nitride layers, 24 and 26, to a thickness of 0.3 $\mu$m using LPCVD at about 580° C. Phosphorous doping can be used to make the Poly-0 layer and other polysilicon layers described hereinafter electrically conductive as needed. The Poly-0 layer can be patterned as shown in FIG. 2B by photolithographic definition and etching (e.g. reactive ion etching) to form electrical connections 28 to each electrode 16 and a lower electrode 30 which will underlie the constricted portion 22 of the channel 14, and to connect these elements to electrically-insulated bond pads 56 formed on the substrate 12 (see FIG. 3A). The lower electrode 30 can be used as a ground plane, or alternately in combination with a superposed upper electrode 48 to provide a vertical electric field for use in separating constituents in a fluid traversing the constricted portion 22 of the channel 14. In some cases, the electrodes 30 and 48 can be used to alter a zeta potential, $\zeta$, of the silicon nitride lining the channel 14 and thereby change the magnitude or direction of the flow of the fluid in the channel 14. After deposition and patterning, the Poly-0 layer can be annealed at a high temperature (e.g. at about 1100° C. for three hours) to reduce any stress therein. A separate annealing step can be performed after deposition and patterning of each subsequent polysilicon layer.

In other embodiments of the present invention, the various electrodes can comprise a metal (e.g. gold, platinum or tungsten) or a metal alloy, or any other electrically-conductive material including, for example, a doped diamond-like carbon (known to the art by various names including amorphous diamond, amorphous carbon and diamond-like carbon) which is depositable using a process such as plasma deposition, laser-assisted deposition or chemical-vapor deposition process. The exact composition for each electrode will depend on whether or not the electrode contacts the fluid, with electrodes contacting the fluid generally being selected for compatibility with the fluid.

Figure 2C:
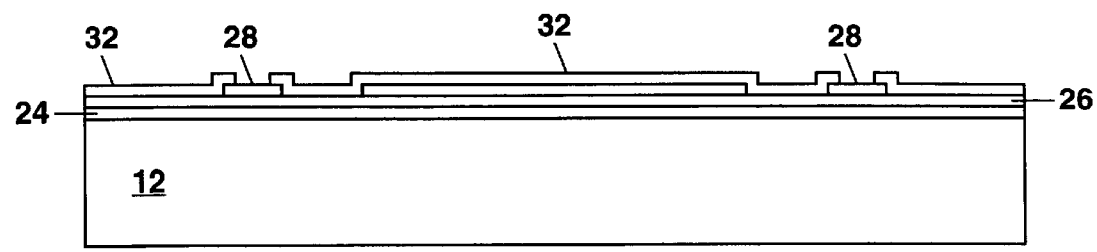

In FIG. 2C, another layer 32 of silicon nitride is deposited over the substrate 12 and patterned to provide openings down do each electrical connection 28 at the location of each electrode 16. This silicon nitride layer 32, which can be deposited by LPCVD, has a thickness in the range of 0.1–2 $\mu$m, and preferably about 0.3 $\mu$m. The silicon nitride layer 32 and a subsequently-deposited silicon nitride layer 34 lining the channel 14 are nonporous and are used to electrically insulate the channel 14 with a dielectric material in order to generate an electroosmotic flow therein. Additionally, the silicon nitride layers, 32 and 34, provide a relatively large zeta potential, $\zeta$, thereby increasing the flow of a fluid in the channel 14 as compared to a polysilicon channel without the silicon nitride lining. Finally, the silicon nitride lining in the channel 14 provides biocompatibility which can be important for certain applications such as cell processing or sorting, or the analysis of biofluids by electrophoresis or chromatography.

Figure 2D:
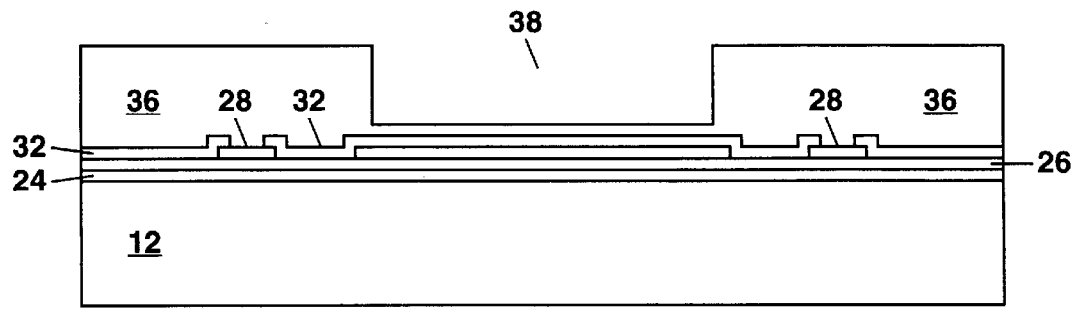

In FIG. 2D, one or more layers of a removable sacrificial material 36 are deposited over the substrate 12 and patterned to form a trench 38 at the location wherein the constricted portion 22 of the channel 14 is to be formed and also to define an overall inside shape 40 of a flow region in the channel 14 (see FIG. 1A). This patterning step can utilize a hard mask (e.g. comprising TEOS) formed over the sacrificial material 36 in preparation for etching the trench 38 and flow region 40 by reactive ion etching. The etching can produce sidewalls of the trench 38 and flow region 40 which are straight or tapered.

The sacrificial material 36 can comprise silicon dioxide or a silicate glass (e.g.. TEOS) which is removable, at least in part, using a selective etchant. The sacrificial material 36 can be deposited over the substrate 12 to a thickness in the range of 1–10 $\mu$m, with the exact thickness and number of layers of the sacrificial material 36 deposited depending upon the size of the flow channel 14 to be formed. Each deposited layer of the sacrificial material 36 is generally about 1–2 $\mu$m thick.

After deposition, the sacrificial material 36 can be planarized, if needed, to provide a relatively uniform thickness for defining the height of the channel 14 outside the constricted portion 22. Such planarization can be performed, for example, by chemical-mechanical polishing as disclosed in U.S. Pat. No. 5,804,084 which is incorporated herein by reference.

In FIG. 2D, the trench 38 can be formed by anisotropically etching down through the sacrificial material 36 (e.g. by reactive ion etching) to leave a predetermined thickness (e.g. 0.1–1 $\mu$m) of the sacrificial material 36 in the trench 38. A further etching step can be used to completely etch through the sacrificial material 36 outside the channel 14, thereby forming the overall inside shape 40 of the flow region in the channel 14, and an overall outside shape 42 for the channel 14 (see FIG. 1A). A portion of the sacrificial material 36 between the inside and outside shapes, 40 and 42, can be separated from the remaining sacrificial material 36 by this etching step so that the separated portion can be encapsulated by a subsequently-deposited silicon nitride layer and retained to strengthen the sidewalls of the channel 14. This encapsulated portion of the sacrificial material 36 is thus prevented from coming into contact with a selective etchant that will later be used to remove the sacrificial material 36 inside the flow region of the channel 14.

Alternately, the sacrificial material 36 can be etched completely through in the trench 38, and another layer of the sacrificial material 36 can be deposited in the trench 38 to a predetermined layer thickness. The selection of particular etching steps for patterning the sacrificial material 36 in the trench 38 will generally depend upon the thickness of the sacrificial material 36 to be provided at the bottom of the trench 38 and the level of accuracy required for this thickness since deposition of the sacrificial material 36 can generally be controlled to a greater accuracy than etching.

Figure 2E:
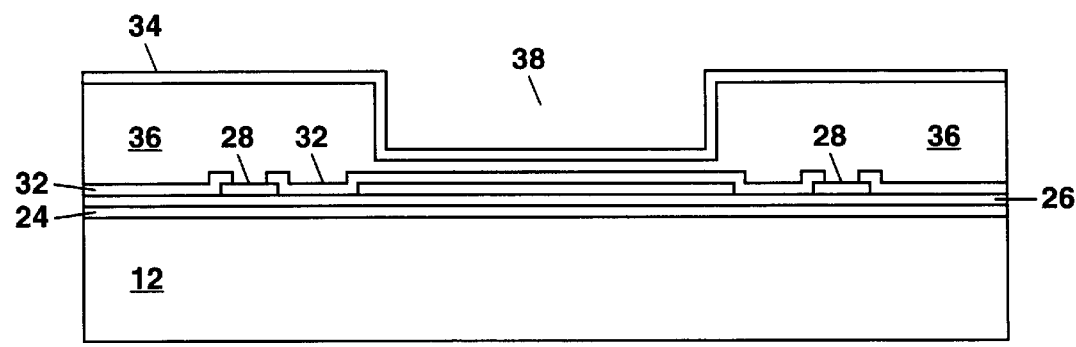

In FIG. 2E, another layer 34 of silicon nitride is conformally deposited over the substrate 12 by LPCVD to form an inner lining of the channel 14 in combination with the underlying silicon nitride layer 32. This silicon nitride layer 34 also encapsulates the portion of the sacrificial material 36 between the inside and outside shapes, 40 and 42, as shown in FIG. 1C. The silicon nitride layer 34 in the first embodiment of the present invention of FIGS. 1A–1C is nonplanar due to deposition within the trench 38; and this forms the constricted portion 22 of the channel 14. The thickness of the silicon nitride layers, 32 and 34, can be the same.

Figure 2F:
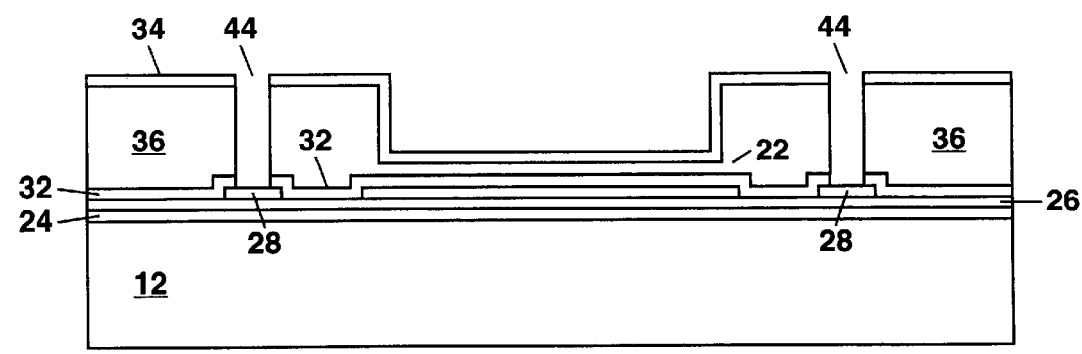

In FIG. 2F, shaped openings 44 are anisotropically etched (e.g. by reactive ion etching) down through the silicon nitride layer 34 and the sacrificial material 36 to expose the electrical connections 28 and to form a mold in the sacrificial material 36 for a subsequent deposition of polysilicon which forms electrodes 16 in the openings 44.

Figure 2G:
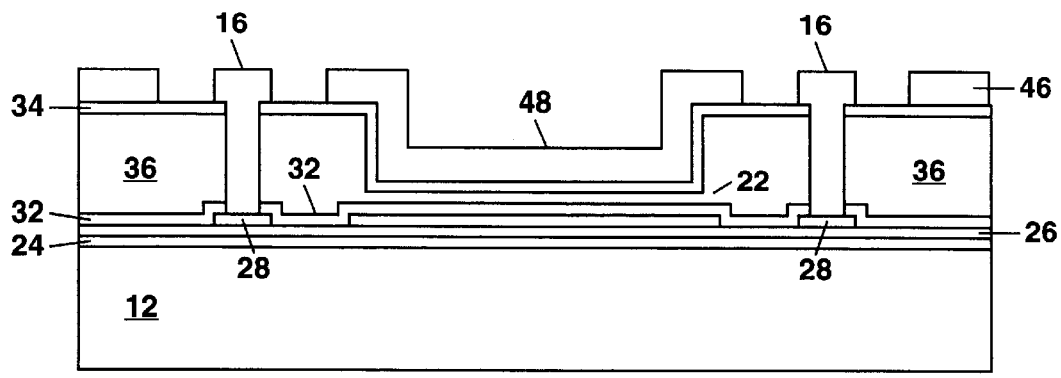

In FIG. 2G, a layer of polysilicon 46 (hereafter Poly-1) is deposited over the substrate 12 and in the shaped openings 44 to form the electrodes 16 which are generally planar and oriented in a direction substantially perpendicular to the substrate 12. These vertically-disposed electrodes 16 are also generally oriented to extend across a majority of the width of the constricted portion 22 without unduly restricting the flow of the fluid (see FIG. 1A).

After deposition, the Poly-1 layer 46 can be patterned to generally conform to the overall outside shape 42 of the channel 14, and can extend the shape 42 slightly outward as the Poly-1 layer 46 covers the encapsulated portion of the sacrificial material 36 and the overlying silicon nitride layer 34 (see FIG. 1C). The Poly-1 layer 46 is also patterned to electrically isolate the electrodes 16 formed therein from the remainder of the Poly-1 layer. The remainder of the Poly-1 layer 46, which can be, for example, 1–2 μm thick, serves to strengthen the top of the channel 14 to withstand changes in pressure therein.

The remainder of the Poly-1 layer 46 can be further patterned to form an upper electrode 48 superposed over the lower electrode 30 as shown in FIG. 2G. When the lower electrode 30 is used as a ground plane, the upper electrode 48 can be either electrically grounded or left floating. When the electrodes 30 and 48 are used, a voltage provided by a power supply (not shown) can be applied between the electrodes, 30 and 48, to alter the flow of the fluid through the channel 14 and move particular constituents therein upwards or downwards, for example, to perform a field-assisted separation of particular constituents in the fluid.

Figure 2H:
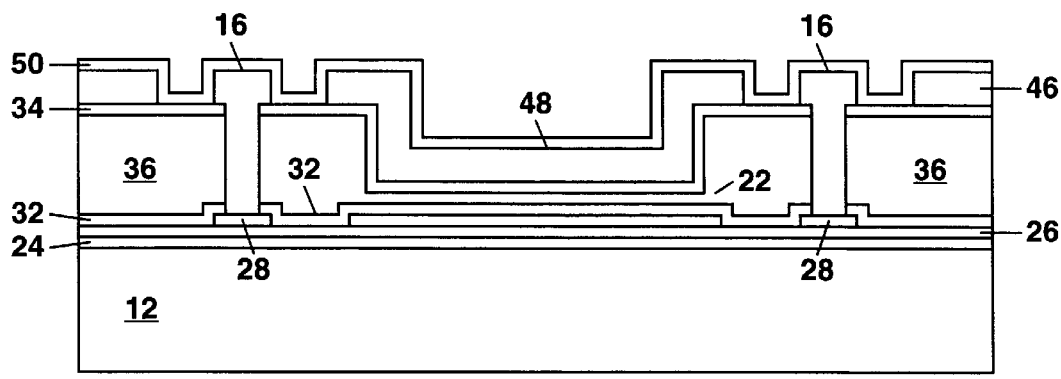
Figure 2I:
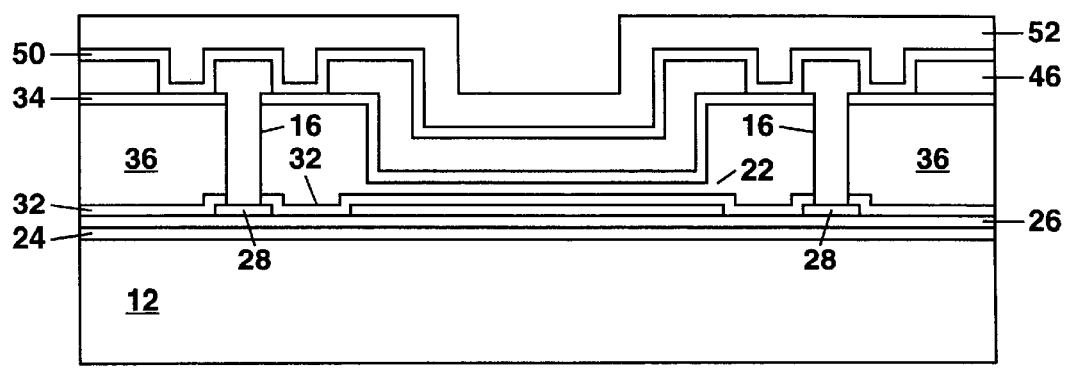

In FIG. 2H, another layer 50 of silicon nitride can be blanket deposited over the substrate 12 to encapsulate the electrodes 16 and 48, and to electrically isolate the electrodes 16 and 48 from a second layer of polysilicon 52 (termed Poly-2) which can be blanket deposited over the substrate 12 to further strengthen the channel 14 (see FIG. 2I). The silicon nitride layer 50 and the Poly-2 layer 52 can be patterned to generally conform to the overall outer shape 42 of the channel 14, with the Poly-2 layer 52 being, for example, 1–3 μm thick.

To complete formation of the channel 14, the sacrificial material 36 must be removed from the flow region 40. This can be done by etching a plurality of etch access holes (not shown), which are typically a few microns in size, down through the various layers to expose the sacrificial material 36 in the flow region 40 for removal of this portion of the sacrificial material 36 by a subsequent etching step.

The etching step utilizes a selective etchant comprising hydrofluoric acid (HF) in liquid or vapor form to etch away the sacrificial material 36 through the etch holes. This etching step generally requires several hours and can be done overnight. The selective etchant removes the sacrificial material 36 from the flow region 40 while not substantially attacking other materials (e.g. polysilicon and silicon nitride) which are chemically resistant to the selective etchant. Once the sacrificial material 36 within the flow region 40 has been removed, the etch access holes can be plugged with LPCVD-deposited silicon nitride. Alternately, the sacrificial material 36 in the flow region 40 can be removed through the entrance and exit ports, 18 and 20, after these ports are formed.

The entrance and exit ports, 18 and 20, can be formed by etching through the back side of the substrate 12 using a deep reactive ion etching process which combines multiple anisotropic etching steps with steps for simultaneously depositing an isotropic polymer/inhibitor to minimize lateral etching. Such a deep etching process is disclosed in U.S. Pat. No. 5,501,893 to Laermer et al, which is incorporated herein by reference. Once the substrate 12 has been etched through, a conventional reactive ion etching step can be used, if needed, to etch through the various deposited layers 24, 26 and 32 in the region of the entrance and exit ports, 18 and 20, to complete formation of the ports, 18 and 20 (see FIG. 1C).

Fluidic connections to the entrance and exit ports, 18 and 20, of the completed device 10 can be made, for example, using capillary tubing (typically a few hundred microns in diameter) attached to the back side of the substrate 12 using an epoxy or elastomeric adhesive. If needed, the holes extending through the substrate 12 to form the entrance and exit ports, 18 and 20, can be stepped as shown in FIG. 1C or tapered at the back side of the substrate 12 for insertion of the capillary tubing.

The apparatus 10 of FIGS. 1A–1C can be used as an electrokinetic pump to provide a flow of a fluid with or without an electric-field separation of particular constituents therein. Such an electrokinetic pump has no moving parts. An electroosmotic mean flow velocity produced in the constricted portion 22 of the channel 14 due to the electroosmotic force generated by a voltage provided by a power supply (not shown) and applied between the electrodes 16 can be calculated using the Helmholtz-Smoluchowski equation:

$$U = \frac{-\varepsilon \zeta E_x}{\mu}$$

where $\epsilon$ is the dielectric constant of the fluid, $\zeta$ is the zeta potential of the silicon nitride lining the channel 14

($\zeta$=0.03V for a pH 6 fluid in contact with silicon nitride), $E_x$ is the electric field produced by a voltage, V, applied between the electrodes 16 separated by a distance, $\Delta x$ ($E_x$=V/$\Delta x$) and $\mu$ is the viscosity of the fluid. As an example, for V=100 volts and $\Delta x$=200 $\mu$m and with water as the fluid ($\epsilon$=7×10$^{-10}$ F-m$^{-1}$ and $\mu$=10–3 kg-m$^{-1}$s$^{-1}$), the calculated mean flow velocity in the constricted portion 22 of the channel 14 is U=10.5 mm-s$^{-1}$. If the constricted portion 22 has lateral dimensions of b=0.1 $\mu$m high and w=200 $\mu$m wide, this mean flow velocity corresponds to a flow rate of Q=Ubw=12.6 nl-min$^{-1}$. The direction of flow of the fluid depends upon the sign of the applied voltage, V. In some instances, an oscillatory voltage, V, can be used, for example, to spatially separate particular constituents in the fluid along the flow region 40.

These calculations illustrate that useful electrokinetic pumping can be obtained with the apparatus 10 of the present invention. Such electrokinetic pumping can be used for many on-chip applications including chemical and biochemical analysis systems, for example, based on electrophoresis or chromatography. Such an electrokinetic pump also has applications for controlling the flow of particular chemicals, for example, to conduct chemical reactions on a micro-scale.

Additionally, if the flow within the device 10 is stopped (e.g. by connecting the exit port to a closed chamber having a moveable wall) then the fluid can generate a hydraulic pressure that scales linearly with the applied voltage, V=$E_x \Delta x$, and is limited only by power dissipation or dielectric breakdown. This hydraulic pressure can be determined by equating the electroosmotic velocity U to a pressure-driven velocity $U_p$ given by:

$$U_p = \frac{b^2}{12\mu}\left(\frac{\Delta P}{\Delta x}\right)$$

where $\Delta P$ is the change in pressure produced by stopping the flow of the fluid. Solving for $\Delta P$, the result is:

$$\Delta P = \frac{12\epsilon\zeta E_x \Delta x}{b^2}$$

For the above example with water as the fluid, stopping the flow in the channel 14 will produce an increase in pressure of $\Delta P$=2.52×10$^6$ N-M$^2$ which is equivalent to a pressure of 25 atmospheres or 367 pounds per square inch (psi). Higher pressures of up to thousands of psi can be produced by increasing the voltage applied across the electrodes 16, with the applied voltage, V, generally being less than or equal to 1000 volts. Thus, significant changes in pressure can be produced with the apparatus 10 of the present invention. This allows the apparatus 10 to be used to form hydraulic actuators as will be described hereinafter. Such hydraulic actuators provide much higher actuation forces (on the order of milliNewtons) than can be realized with conventional electrostatic actuators which typically produce forces on the order of microNewtons.

FIGS. 3A–3D show a schematic plan view and cross-section views of a second embodiment of the apparatus 10 of the present invention. This apparatus 10 is useful for separating particular constituents in a flowing fluid using a plurality of separation electrodes 54, 54' and 54" which are formed about the channel 14 and independently activated by voltages provided through contact pads 56 and electrical wiring 58. The contact pads 56 can comprise a deposited and patterned metallization (e.g. aluminum or an aluminum alloy, or gold). The electrical wiring 58 can be formed either from the Poly-0 layer underlying the channel 14, from a polysilicon layer (e.g. the Poly-1 or Poly-2 layers) overlying the channel 14, from a deposited and patterned metallization, or from a combination thereof.

Figure 3B:
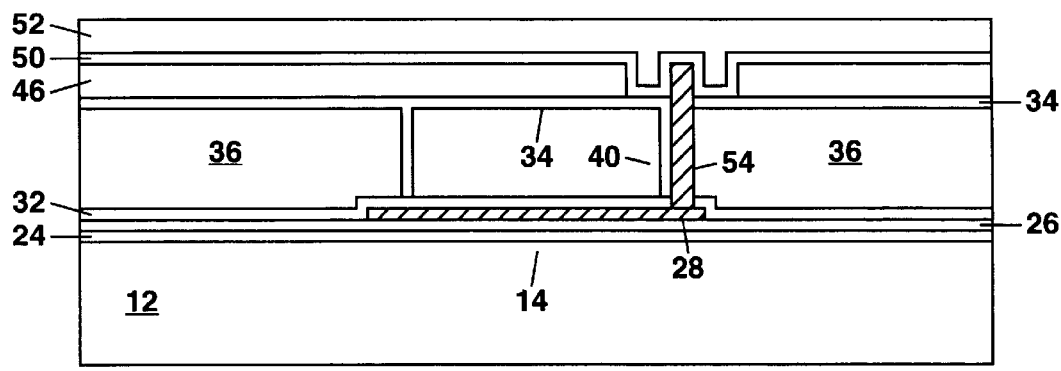
FIGS. 3B, 3C and 3D show schematic cross-section views of the device of FIG. 3A along the section lines 3—3, 4—4 and 5—5, respectively.

The electrodes 54 comprise electrical conductors (e.g. doped polysilicon) disposed about one side and the bottom of the channel 14 as shown in FIG. 3B to provide electric fields that can be used to separate charged particles (i.e. ions) in the fluid by moving the particles towards or away from particular electrodes 54 depending upon the sign of the charge on the particles and the voltage applied to the electrodes 54. This movement can advance or retard the flow of particular ionic constituents in the fluid, or provide for a lateral separation of the constituents.

The electrodes 54' act similarly to the electrodes 54 but are oppositely oriented. A third type of electrodes 54" comprising vertically-disposed electrical conductors can provide for a horizontal separation of the constituents in the fluid based on charge and applied voltage. Although not shown, additional electrodes similar to the electrodes 54" but comprising horizontally-disposed electrical conductors located above and below the channel 14 can be used to provide for a vertical separation of the constituents in the fluid. Static or oscillatory voltages can be independently applied to each of the electrodes 54, 54' and 54" through the various contact pads 56 so that the apparatus 10 can be used to provide an electrophoretic separation of constituents of a fluid therein.

The device 10 of FIGS. 3A–3D can be operated with an external flow of the fluid to be analyzed provided by an electrokinetic pump (e.g. a capillary electrokinetic pump as disclosed in U.S. Pat. No. 6,013,164 which is incorporated herein by reference), or by an on-chip electrokinetic pump similar to that described previously with reference to FIGS. 1A–1C. An on-chip electrokinetic pump can be formed in the same channel 14 containing the electrodes 54, 54' and 54", or in a different channel which is in fluid communication with the channel 14 of FIG. 3A. The apparatus 10 of FIGS. 3A–3D can even be operated so that a voltage can be applied between certain of the electrodes 54 and 54' can generate an electrokinetic flow of the fluid, while other of the electrodes 54, 54' and 54" are used for separating particular constituents in the fluid.

Fabrication of the surface-micromachined apparatus 10 of FIGS. 3A–3D can be performed using a series of deposition and patterning steps similar to those described previously with reference to FIGS. 2A–2I. Briefly, the substrate 12 is initially prepared by forming a thermal oxide layer 24 and depositing a silicon nitride layer 26 as described with reference to FIG. 2A. A first polysilicon layer 28 (i.e. the Poly-0 layer) is then deposited over the substrate 12 as described with reference to FIG. 2B and can be patterned to form the electrical wiring 58 and horizontally-disposed electrical conductors used in forming the electrodes 54 (see FIG. 3B). The Poly-0 layer can also be used to form a support base for the electrodes 54' and 54" to connect these electrodes to the electrical wiring 58 (see FIGS. 3C and 3D). A second silicon nitride layer 32 can then be blanket deposited over the substrate 12 as described with reference to FIG. 2C and can be patterned to provide openings down to the Poly-0 layer at the locations of vertically-disposed electrical conductors used to form the electrodes 54, 54' and 54". The second silicon nitride layer 32 also serves to line the bottom of the channel 14 being formed.

Figure 3C:
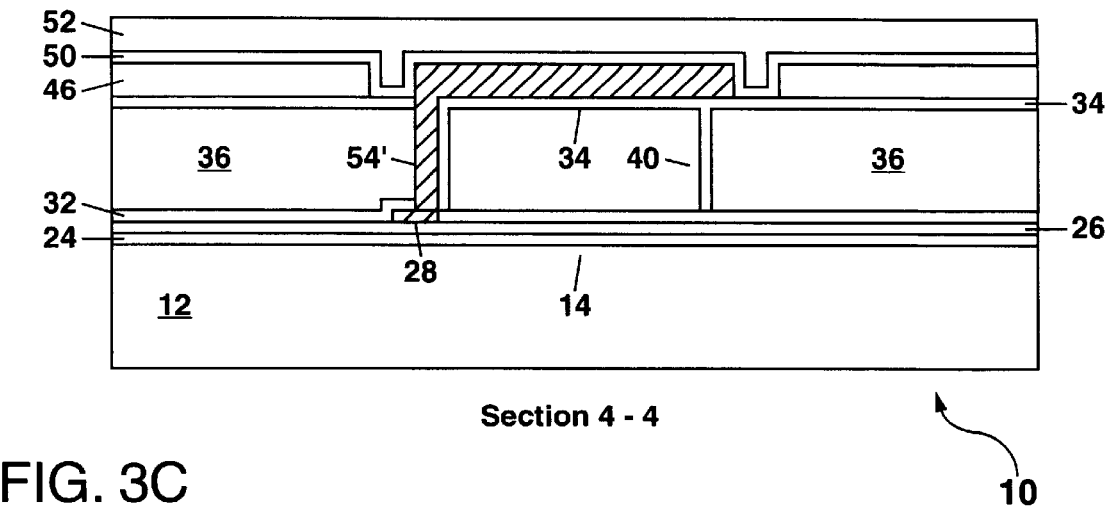
Figure 3D:
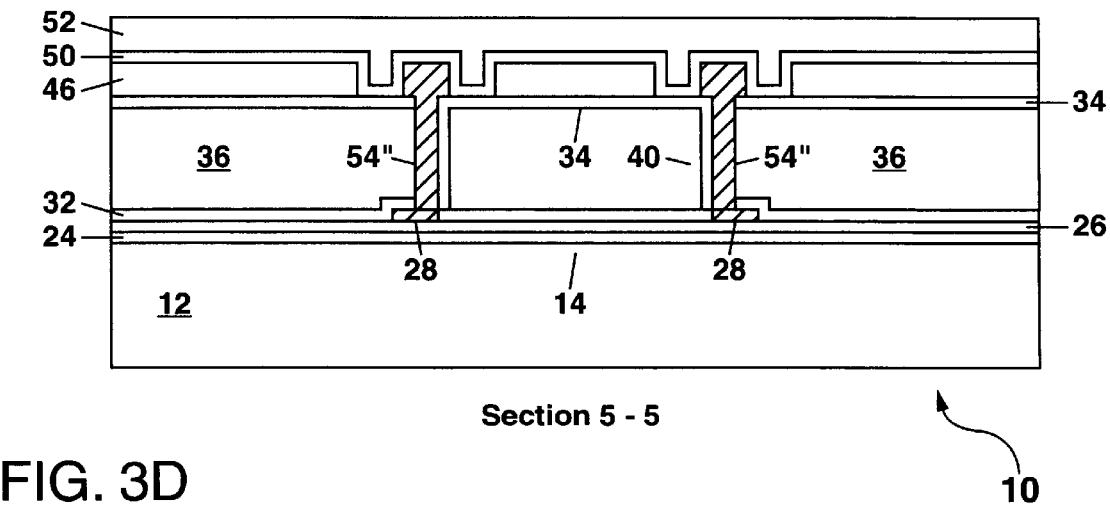

One or more layers of the sacrificial material 36 are then deposited over the substrate 12 and optionally planarized as described with reference to FIG. 2D. The height of the channel 14 can be locally adjusted as needed by etching down partially through the sacrificial material 36. When an electrokinetic pump is to be formed in a portion of the channel 14 containing the electrodes 54, 54' and 54", the height of the channel 14 can be reduced at the location of the electrokinetic pump. Elsewhere, the channel 14 can have a larger height as shown in FIGS. 3B–3D. An annular trench can be etched through the sacrificial material to define the flow region 40 of the channel 14.

The sidewalls and top of the channel 14 are lined, at least in part, with a third layer 34 of silicon nitride which is deposited over the substrate 12 and inside the annular trench which defines the flow region 40. The third silicon nitride layer 34 has been previously described with reference to FIG. 2E.

After deposition of the third silicon nitride layer 34, shaped openings 44 are etched through the sacrificial material down to the Poly-0 layer at the locations of the vertically-disposed electrical conductors for forming the electrodes 54, 54' and 54". These vertically-disposed electrical conductors are formed by a subsequent deposition of the Poly-1 layer 46 as described with reference to FIG. 2G. After deposition, the Poly-1 layer 46 is patterned to electrically isolate the electrodes 54, 54' and 54" from the remainder of the Poly-1 layer.

A third layer 50 of silicon nitride can be blanket deposited over the substrate 12 and sealed to the underlying silicon nitride layer 34 as previously described with reference to FIG. 2G. The Poly-2 layer 52 can then be deposited over the substrate 12 as previously described with reference to FIG. 2I to further strengthen the channel 14 to withstand changes in pressure therein. To complete formation of the apparatus 10 of FIGS. 3A–3D, the sacrificial material 36 within the channel 14 is removed with a selective etchant as described previously.

Figure 4:
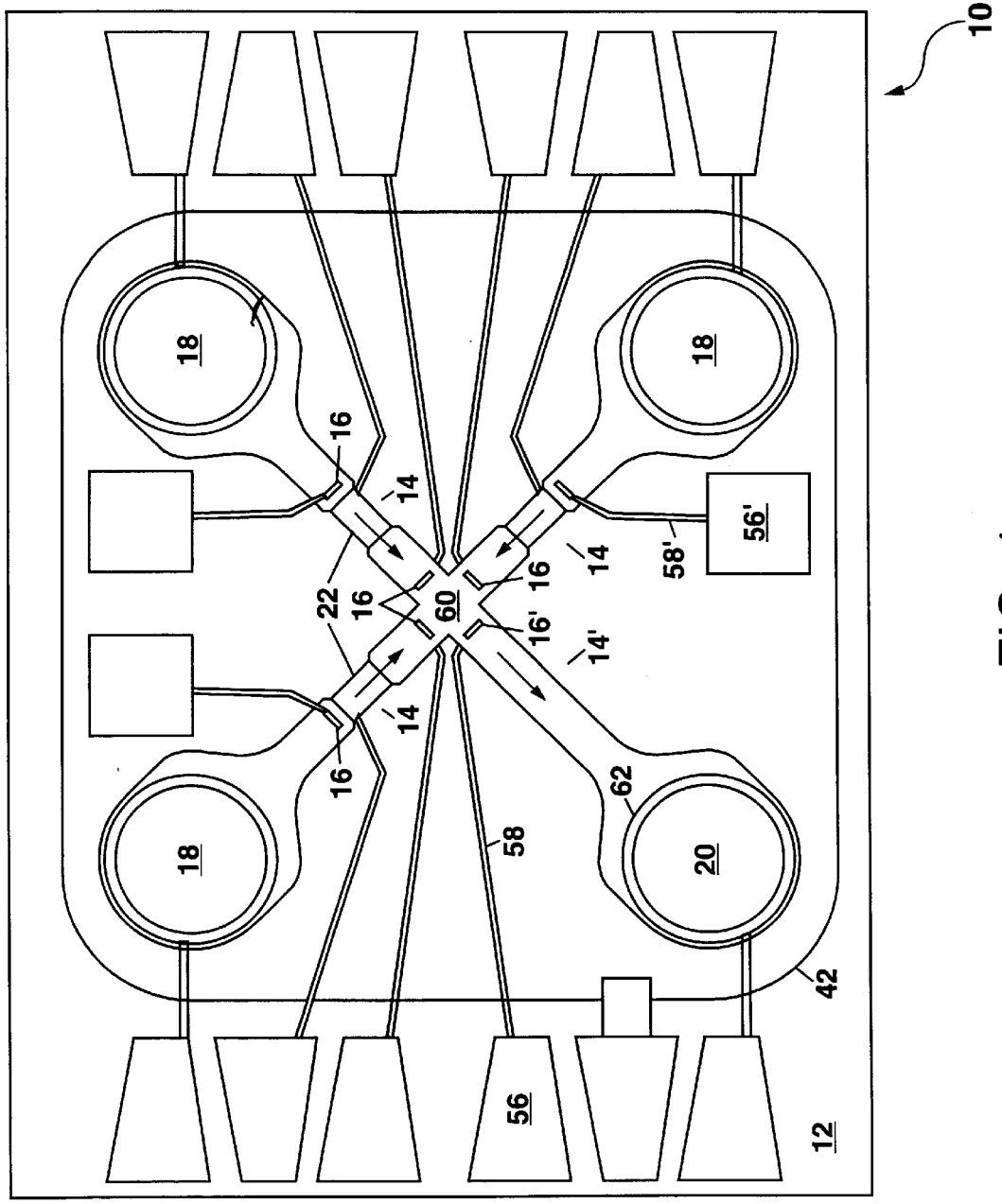
FIG. 4 shows a schematic plan view of a third embodiment of the present invention.

A third embodiment of the present invention is shown schematically in the plan view of FIG. 4. In this embodiment of the present invention, the apparatus 10 with an X-shaped channel structure is designed to electrophoretically separate constituents from a fluid slug (not shown) introduced into the apparatus 10 at one or more entrance ports 18. The apparatus 10 can also be used to conduct chemical reactions on a micro-scale with reactants being introduced into the apparatus 10 at the entrance ports 18 and with resultant chemical reaction products being directed towards exit port 20. An electrophoretic separation of the resultant products can also be performed using the apparatus 10. In the device 10 of FIG. 4, each entrance port 18 has an associated electrokinetic pump comprising electrodes 16 surrounding a constricted channel portion 22. The structure of the electrokinetic pumps in FIG. 4 has been described previously with reference to FIGS. 1A–1C.

Upon activation of each electrokinetic pump in FIG. 4 by applying a first voltage from a power supply to a particular set of electrodes 16 through a pair of contact pads 56 and 56' and associated wiring 58, a fluid slug in each channel 14 can be pumped through the constricted portion 22 and towards an intersection 60. Upon reaching the intersection 60, a second voltage can be applied between electrode 16' and one or more of the electrodes 16 to urge the slug across the intersection 60 and into another channel 14' wherein the constituents in the fluid slug can be electrophoretically separated under the influence of an electric field produced by a third voltage applied between the electrode 16' and a ring electrode 62 formed about the exit port 20 of separation channel 14'.

Fabrication of the separation device 10 of FIG. 4 can be performed as described previously with reference to FIGS. 2A–2I. Contact pads 56 can be formed on the substrate 12, with the wiring 58 connecting the pads 56 to particular electrodes 16, 16' and 60 generally being formed from the Poly-0 layer. The contact pads 56' and associated wiring 58 connected thereto can comprise, for example, a deposited and patterned metallization provided above the Poly-2 layer 52 and insulated therefrom by an intervening passivation layer (e.g. comprising silicon nitride, silicon dioxide, a silicate glass or a spin-on glass).

Figure 5A:
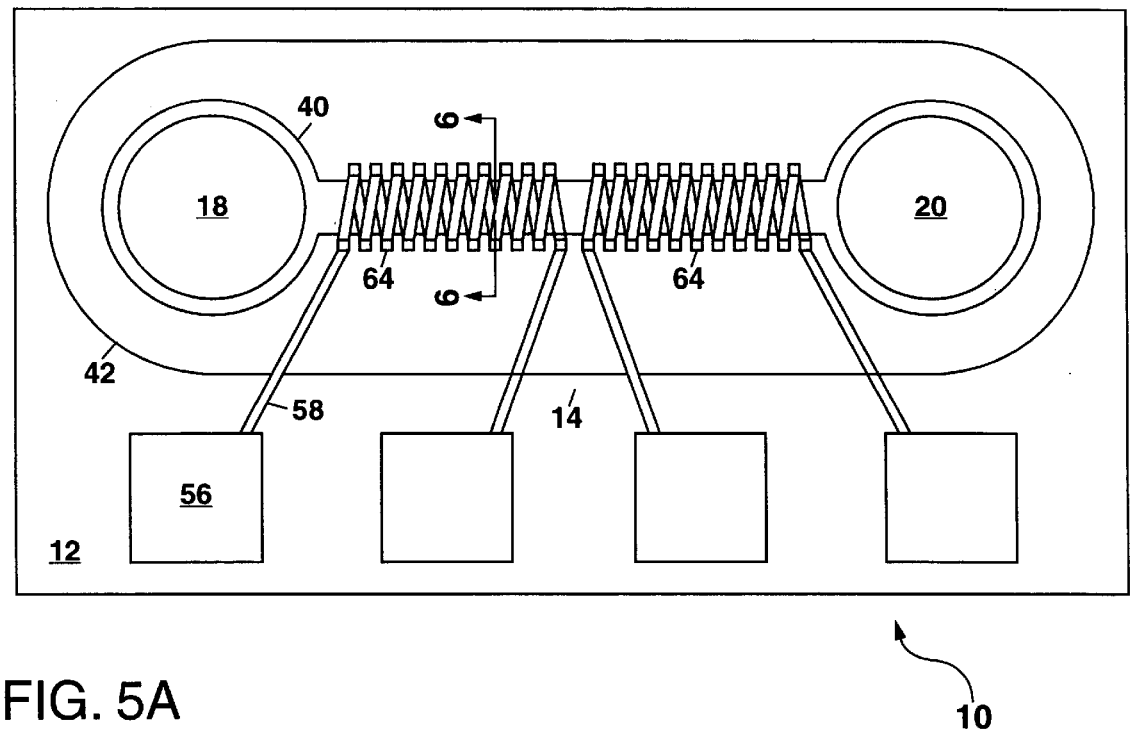
FIG. 5A shows a schematic plan view of a fourth embodiment of the present invention.
Figure 5B:
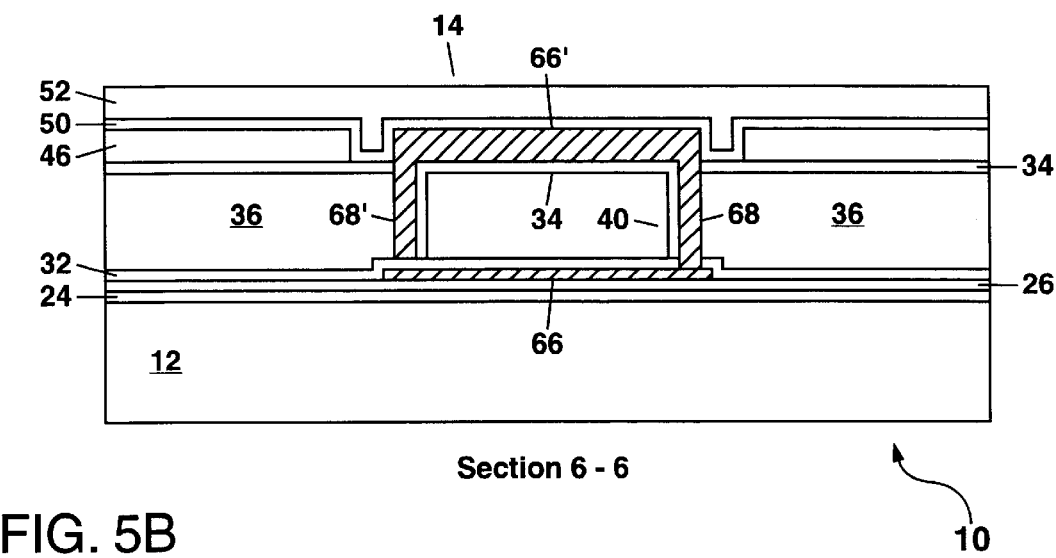
FIG. 5B shows a schematic cross-section view of the device of FIG. 5A along the section line 6—6.

FIGS. 5A and 5B schematically illustrate a fourth embodiment of the present invention which utilizes an electromagnetic field produced by one or more coils 64 to generate a flow of a fluid or particular constituents therein along a channel 14, or to spatially separate particular constituents of the fluid through an electromagnetic field interaction, or to pressurize the fluid in the channel 14 or in a closed chamber connected to the channel 14. This embodiment of the present invention is particularly suited for use with fluids having constituents comprising ions (e.g. an electrolyte) or magnetic moments.

In FIG. 5A, each coil 64 comprises a plurality of turns of an electrical conductor formed about the channel 14, with each turn further comprising a plurality of horizontally-disposed electrical conductors 66 and vertically-disposed electrical conductors 68 which are generally located outside the flow region 40 of the channel 14, with each horizontally-disposed electrical conductor 66 being electrically connected to a pair of the vertically-disposed electrical conductors 68 to form an open ring structure. The channel 14 is generally rectangular and can optionally include a constricted portion 22 as described previously.

Fabrication of the apparatus 10 of FIGS. 5A and 5B with one or more coils 64 surrounding the channel 14 can be performed using the steps described previously with reference to FIGS. 2A–2I with slight modifications as described hereafter. Referring to FIG. 5B, which shows a schematic cross-section view to illustrate how each turn of the coil 64 can be formed, a lower horizontally-disposed electrical conductor 66 can be formed from the Poly-0 layer below the nitride layer 32 which lines the bottom of the channel 14. The lower conductor 66 is electrically connected to a vertically-disposed electrical conductor 68 formed from the Poly-1 layer 46. The Poly-1 layer 46 is also used to form an upper horizontally-disposed electrical conductor 66' overlying the silicon nitride layer 34 which lines the top and sides of the channel 14, and is attached to the other end of the conductor 68 and is further attached to another vertically-disposed electrical conductor 68' which is not attached to the conductor 66, but is offset slightly therefrom. The conductors 66', 68 and 68' can be simultaneously formed from deposition of the Poly-1 layer 46. Each adjacent turn of the coil 64 is formed similarly with the adjacent turns of the coil being connected to each other by the vertically-disposed conductor 68'.

In FIG. 5A, each coil 64 can be separately activated by an electrical current provided by a power supply (not shown), with the electrical current flowing through the contact pads 56 and electrical wiring 58 connected to each coil 64. The electrical current produces a longitudinal electromagnetic field (also termed a magnetic field) within the channel 14 which can interact with constituents of a fluid introduced therein through entrance port 18 to urge the constituents and fluid along the channel 14 at different rates and in different directions based on the charge or magnetic moment of the constituents. Those skilled in the art will understand that a spatial separation of constituents in a flowing fluid produced by the apparatus 10 of FIGS. 5A and 5B will produce a temporal separation in the constituents arriving at a specific point (e.g. where a detector is placed to differentiate among the constituents based on their arrival time). Optical detection of the constituents is also possible by omitting the Poly-1 and Poly-2 layers from a portion of the channel 14 since the remaining silicon nitride layers 34 and 50 are transparent to light.

Additional coils or electrodes (not shown) can be formed oriented about the channel 14 to urge particular constituents to move in one or more lateral directions perpendicular to the direction of the flow of the fluid in the channel 14. These electrodes can be similar to those described previously with reference to FIGS. 1A–1C and 3A–3D, while the additional coils can comprise a single turn formed from one or more polysilicon layers. For example, the Poly-0 layer can be patterned to form a single-turn open coil in the plane of the substrate 12 and below the channel 14. As another example, the Poly-1 layer 46 can be patterned to form a single-turn open coil in the plane of the substrate 12 and above the channel 14. Additionally, the Poly-1 layer 46 can be patterned to form in combination with the Poly-0 layer 28 a single- or multi-turn coil oriented perpendicular to the plane of the substrate 12 and aligned along one or both sides of the channel 14 in a direction perpendicular to the direction of flow in the channel 14.

Figure 6:
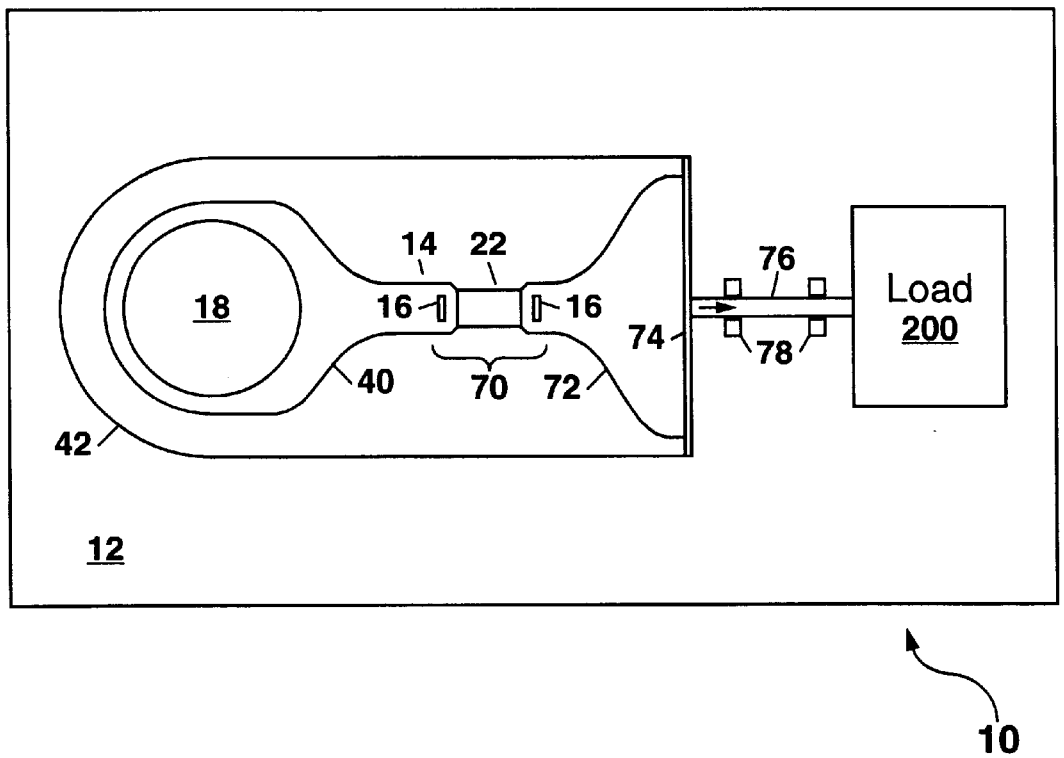
FIG. 6 shows a schematic plan view of a fifth embodiment of the present invention.

A fifth embodiment of the present invention is schematically illustrated in FIG. 6. This embodiment of the present invention is a hydraulic actuator 10 formed by an electrokinetic pump 70 in fluid communication with a closed chamber 72 having at least one wall 74 which is moveable or deformable in response to a change in pressure of a fluid introduced into the channel 14. In FIG. 6, the electrokinetic pump 70, which comprises a pair of electrodes 16 on either side of a constricted portion 22 of a channel 14, operates by an electroosmotic force produced upon the application of a voltage between the electrodes 16 as described previously with reference to FIGS. 1A and 1B.

The closed chamber 72 in FIG. 6 can be formed by expanding the flow region 40 of the channel 14 outward in an arbitrary shape on one side of the electrokinetic pump 70. The chamber 72 includes one or more moveable walls 74 which can be formed from a thin layer or membrane of a deposited material (e.g. silicon nitride, polysilicon, a metal or a metal alloy). The wall 74 can be formed either by depositing the wall material into a narrow trench (e.g. $\leq 1$ $\mu$m wide) etched down into the sacrificial material 36, or by depositing a thin layer (e.g. $\leq 1$ $\mu$m thick) of the wall material over the sacrificial material 36 which has been previously deposited and patterned to define the shape of the chamber 72. As an example, the silicon nitride layers 34 or 50 or both previously described with reference to FIGS. 2D and 2G can be used to form the wall 74. The top and bottom edges of the wall 74 are adhered to other of the material layers forming the device 10 (e.g. to the silicon nitride layer 32 at the bottom of the wall 74 and to the Poly-1 and/or Poly-2 layers at the top of the wall 74). The moveable wall 74 can be, for example, up to about 10 $\mu$m high and 0.05–1 mm wide.

In operation, the electrokinetic pump 70 moves a fluid (e.g. water or acetonitrile) into the channel 14 and closed chamber 72 which have been previously evacuated. As the fluid is further pressurized by the electrokinetic pump 70, the increase in pressure of the fluid in the chamber 72 acts to move or deform the wall 74, thereby producing a horizontal displacement (i.e. in the plane of the substrate 12) of an actuator arm 76 connected to the wall 74. This displacement of the actuator arm 76 is further communicated to a load 200 with which the actuator arm 76 is operatively connected.

In FIG. 6, the actuator arm 76 is generally suspended above the substrate 12 and can be formed, for example, from one or more of the polysilicon and silicon nitride layers used to form the remainder of the device 10. A plurality of guides 78 comprising polysilicon or silicon nitride can also be used to restrict movement of the actuator arm 76 to a particular direction. In other embodiments of the present invention, a lever, linkage, compliant mechanism or the like can be substituted for the actuator arm 76 depending upon a particular force vector to be applied to drive the load 200, and depending on whether the force vector is to be redirected at some arbitrary angle (e.g. 90°) out of the plane of the substrate.

A compliant mechanism is disclosed in U.S. Pat. No. 6,175,170 to Kota et al, which is incorporated herein by reference, is particularly useful for multiplying the displacement of the wall 74 which will generally be on the order of one micron or less, with the exact displacement depending upon the size and stiffness of the wall 74 and the pressure change produced by the voltage applied between the electrodes 16.

The load 200 can be any type of micromechanical device known to the art. The drive force provided by the hydraulic actuator 10 can be directed towards the load 200 (e.g. by pressurizing the chamber 72), away from the load 200 (e.g. by depressurizing the chamber 72). The application of a cyclic voltage to the electrokinetic pump 70 can be used to produce a reciprocating motion of the wall 74 and actuation arm 76 for driving the load 200.

Figure 7A:
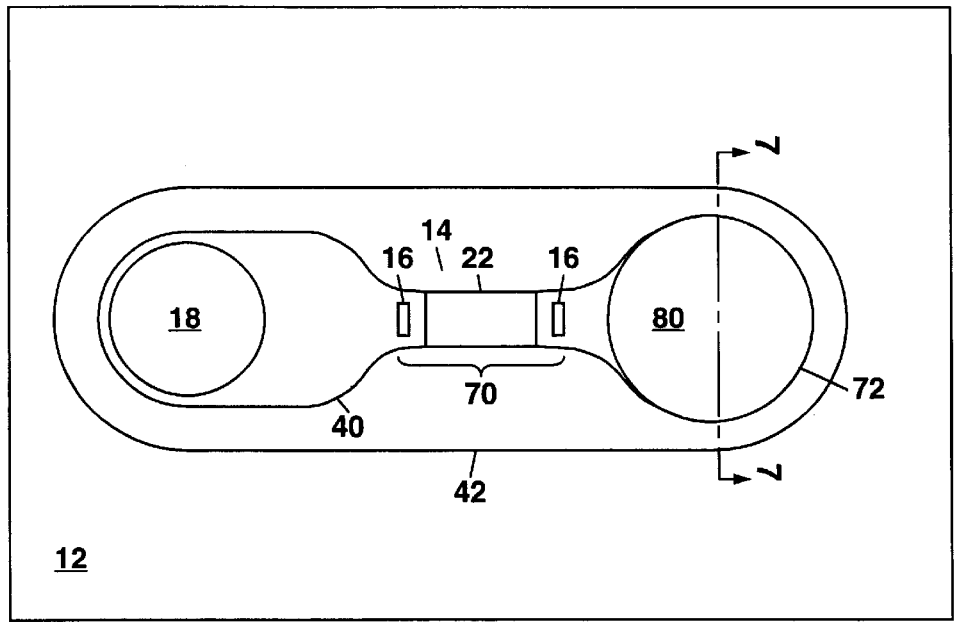
FIG. 7A shows a schematic plan view of a sixth embodiment of the present invention.
Figure 7B:
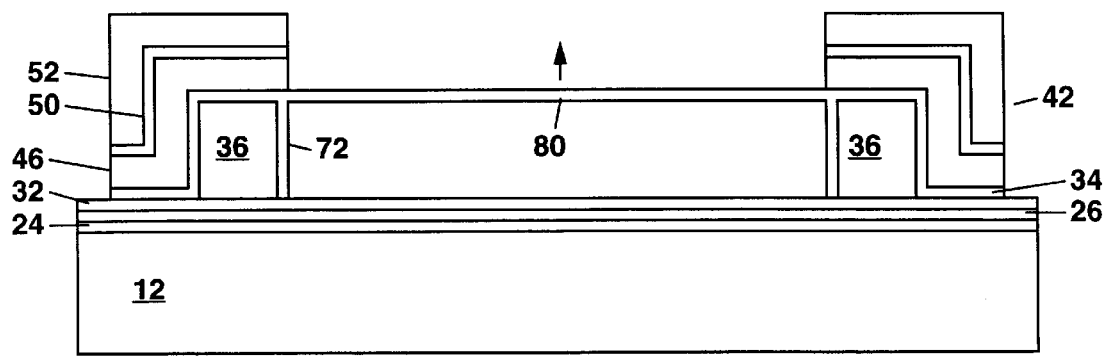
FIG. 7B shows a schematic cross-section view of the device of FIG. 7A along the section line 7—7.

FIGS. 7A and 7B show a sixth embodiment of the present invention in the form of an out-of-plane hydraulic actuator 10. The out-of-plane actuator 10 comprises an electrokinetic pump 70 and a closed chamber 72 having an upper wall 80 in the form of a circular diaphragm oriented in the plane of the substrate 12. The upper wall 80 is moveable upwards in response to an increase in the pressure of a fluid in the chamber 72 and downwards in response to a decrease in the pressure of the fluid.

The apparatus 10 of FIGS. 7A and 7B is has a construction similar to the device of FIGS. 1A–1C with modifications to omit the exit port 20 and thereby form the closed chamber 72 which has been enlarged (e.g. to provide a diameter for the wall 80 which can be in the range of 0.1–10 mm). Additionally, the layers 46, 50 and 52 shown in FIG. 1C have been omitted over the closed chamber 72 in the cross-section view of FIG. 7B so that the silicon nitride layer 34 forms the moveable upper wall 80. In this device 10, motion of the wall 80 in response to a change in pressure of the fluid in the chamber 72 is out of the plane of the substrate 12 (i.e. at an angle of 90° to the plane of the substrate 12). However, the motion of the wall 80 can be operatively coupled to a load 200 at any arbitrary angle of 0 to 90° with respect to the substrate 12 through a suitable coupling mechanism in the form of an actuator arm, lever, linkage, compliant mechanism or a combination thereof. The coupling mechanism can be fabricated on the substrate 12 using the same surface micromachining steps used to fabricate the actuator 10, or by using a series of additional surface micromachining processing steps for depositing and patterning additional layers of polysilicon, silicon nitride or sacrificial material 36.

In some instances, it is desirable to convert the vertical motion of the wall 80 into horizontal motion (i.e. in-plane motion) that is substantially in the plane of the substrate 12.

Figure 8A:
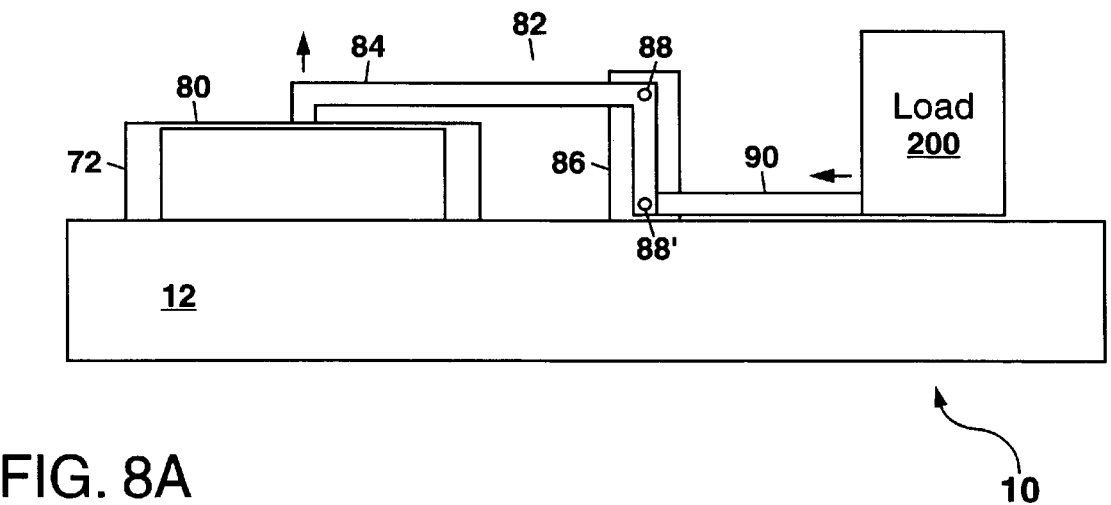
FIGS. 8A and 8B schematically illustrate how a linkage can be used with the device of FIGS. 7A and 7B to convert out-of-plane motion into in-plane motion for coupling to a load.
Figure 8B:
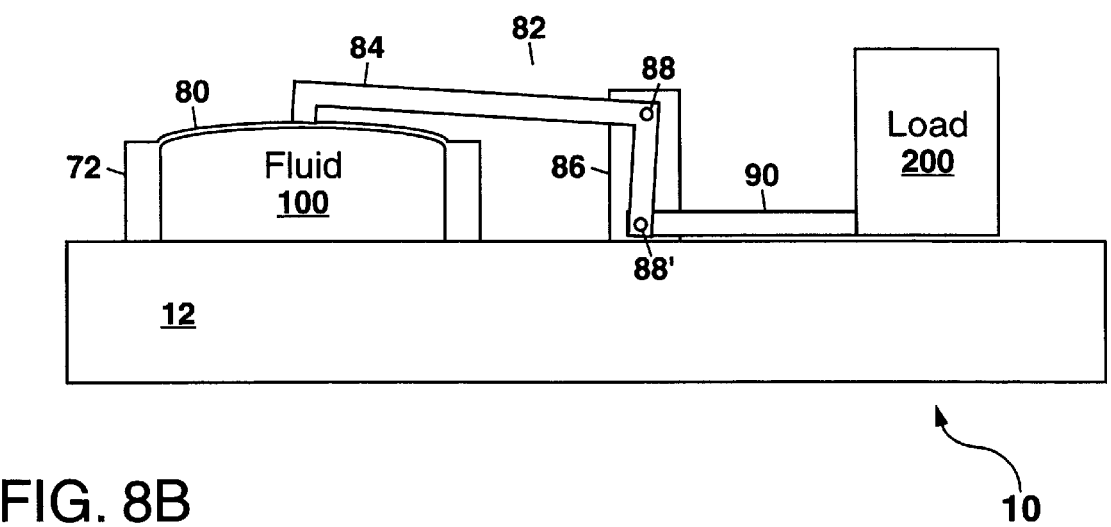

This can be done, for example, through the use of a linkage 82 as schematically illustrated in FIGS. 8A and 8B. FIG. 8A shows the device 10 in its initial fabricated position; and FIG. 8B shows the device 10 after actuation by pressurizing the closed chamber 72 with a fluid 100 to move the wall 80 upwards. The linkage 82 comprises a lever arm 84 connected to the moveable wall 80 and further rotatably connected to a support 86 through a pin joint or torsional hinge 88. The lever arm 84 is further connected to a linkage arm 90 through a second pin joint or torsional hinge 88'. Rotation of the lever arm 84 about the pin joint or torsional hinge 88 acts to move the linkage arm 90 in a horizontal direction (i.e. in the plane of the substrate 12) as shown in FIG. 8B. If needed, a compliant mechanism (not shown) can be connected between the load 200 and the linkage arm 90 to multiply the displacement of the linkage arm 90 (e.g. by a factor of 10 or more) with a corresponding reduction in force.

The linkage 82 of FIGS. 8A and 8B can also be used with the in-plane actuator 10 of FIG. 6 to convert horizontal motion of the wall 72 into motion at an angle (e.g. 90°) to the substrate 12. This can be done by connecting the moveable wall 72 of the device 10 of FIG. 6 at the right-hand side of the linkage 82 of FIGS. 8A and 8B, with the left-hand side of the linkage 82 being connected to the load 200.

The direction of flow of the fluid can be reversed by reversing the direction of the voltage from a power supply (not shown) applied to the electrodes 16 of the electrokinetic pump 70. This will reduce the pressure in the closed chamber 72 thereby moving the wall 80 downward and reversing the motion of the linkage 82. Alternately, the voltage can be removed from the electrodes 16 to allow the wall 80 to naturally return to its initial undeflected position, thereby moving the linkage 82 backward. Those skilled in the art will understand that other arrangements are possible to convert vertical motion of the wall 80 into horizontal motion for driving a load 200.

Other applications and variations of the present invention will become evident to those skilled in the art. For example, the channel 14 can include a plurality of shaped columns (also termed posts or micro-posts) arranged in an array to increase a total surface area within the channel 14 as disclosed in U.S. Pat. No. 6,096,656 to Matzke et al, which is incorporated herein by reference. Such an array of microposts, which can be formed by patterning the sacrificial material 36 in the channel 14 to form the posts prior to depositing the silicon nitride layer 34 which covers the posts and encapsulates part of the sacrificial material 36 so that it is not later removed by the selective etchant. The encapsulated sacrificial material 36 lined with silicon nitride effectively forms a packed channel 14 which provides an increased surface area. The increased surface area can be advantageous for electrokinetic pumping, electrophoresis or chromatography since the movement and separation of different constituents in the fluid can be enhanced by interaction with the increased surface area. Furthermore, a packed channel 14 can provide an increased stationary phase interaction which can reduce the length required for the channel 14 for certain applications.

The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A surface-micromachined apparatus, comprising:
   (a) a microchannel formed on a substrate from a plurality of deposited and patterned layers of polycrystalline silicon and silicon nitride, with the silicon nitride at least partially lining the microchannel, and with the microchannel including a constricted portion having a lateral dimension smaller than the lateral dimension of the remainder of the microchannel; and
   (b) means for generating an electroosmotic force or electromagnetic field in the microchannel.

2. The apparatus of claim 1 wherein the substrate comprises silicon.

3. The apparatus of claim 1 wherein the constricted portion has a height that is smaller than the height of the remainder of the microchannel.

4. The apparatus of claim 3 wherein the height of the constricted portion is in the range of 0.1–1 microns.

5. The apparatus of claim 4 wherein the constricted portion of the microchannel has an overall width in the range of 0.05–10 millimeters.

6. The apparatus of claim 1 wherein the microchannel and the constricted portion thereof are defined by a removable sacrificial material.

7. The apparatus of claim 6 wherein the sacrificial material comprises silicon dioxide or a silicate glass.

8. The apparatus of claim 1 wherein the silicon nitride lining has a thickness in the range of 0.1–2 microns.

9. The apparatus of claim 1 wherein the means for generating the electroosmotic force or electromagnetic field in the microchannel comprises a plurality of electrodes for generating an electric potential within the microchannel in response to a voltage provided to the electrodes.

10. The apparatus of claim 9 wherein the voltage is 1000 volts or less.

11. The apparatus of claim 9 wherein the electrodes comprise an electrically-conductive material selected from the group consisting of polycrystalline silicon, a metal, a metal alloy, and carbon.

12. The apparatus of claim 9 wherein a first electrode is located proximate to one end of the constricted portion of the microchannel, and a second electrode is located proximate to the other end of the constricted portion of the microchannel.

13. The apparatus of claim 12 wherein at least one additional electrode of the plurality of electrodes is located in or proximate to the microchannel between the first and second electrodes.

14. The apparatus of claim 1 wherein the microchannel includes an entrance port for introducing a fluid into the microchannel.

15. The apparatus of claim 14 wherein the fluid comprises an electrolyte.

16. The apparatus of claim 14 wherein the fluid within the microchannel is moveable in response to the generated electroosmotic force or the electromagnetic field.

17. The apparatus of claim 14 wherein the electroosmotic force or electromagnetic field pressurizes the fluid within the microchannel.

18. A surface-micromachined apparatus, comprising:
   (a) a microchannel formed on a substrate from a plurality of deposited and patterned layers of polycrystalline silicon and silicon nitride, with the silicon nitride at least partially lining the microchannel; and
   (b) a coil formed about a portion of the microchannel for generating an electroosmotic force or electromagnetic field in the microchannel.

19. The apparatus of claim 18 wherein the coil is activated by an electrical current to produce the electromagnetic field in the microchannel.

20. The apparatus of claim 18 wherein the portion of the microchannel about which the coil is formed has a rectangular cross-section shape.

21. The apparatus of claim 20 wherein the portion of the microchannel about which the coil is formed has a height that is smaller than a width thereof.

22. A surface-micromachined apparatus, comprising:
(a) a microchannel having an entrance port for introducing a fluid into the microchannel and an exit port, with the microchannel being formed on a substrate from a plurality of deposited and patterned layers of polycrystalline silicon and silicon nitride, and with the silicon nitride at least partially lining the microchannel; and
(b) means for generating an electroosmotic force or electromagnetic field in the microchannel to pump the fluid through the microchannel from the entrance port to the exit port.

23. The apparatus of claim 22 wherein at least one of the entrance port and the exit port extend through the thickness of the substrate.

24. A surface-micromachined apparatus, comprising:
(a) a microchannel formed on a substrate from a plurality of deposited and patterned layers of polycrystalline silicon and silicon nitride, with the silicon nitride at least partially lining the microchannel, and with the microchannel having an entrance port for introducing a fluid into the microchannel;
(b) a closed chamber connected to the microchannel, with the chamber having a wall thereof which is moveable in response to a change in pressure of the fluid; and
(c) means for generating an electroosmotic force or electromagnetic field in the microchannel for pressurizing the fluid within the microchannel and thereby moving the wall of the closed chamber.

25. The apparatus of claim 24 further including means, operatively connected to the moveable wall of the chamber, for transmitting motion of the moveable wall to a load.

26. The apparatus of claim 25 wherein the motion transmitting means is selected from the group comprises an actuator arm, a lever, a linkage, a compliant mechanism or a combination thereof.

27. The apparatus of claim 24 wherein the moveable wall of the chamber is oriented in the same plane as the substrate, and the motion transmitting means transmits motion of the moveable wall to the load in an out-of-plane direction that is at an angle to the plane of the substrate.

28. The apparatus of claim 24 wherein the moveable wall of the chamber is oriented substantially perpendicular to the plane of the substrate, and the motion transmitting means transmits motion of the moveable wall to the load in an in-plane direction that is in the plane of the substrate.

29. The apparatus of claim 28 wherein the angle is substantially equal to 90 degrees.

30. A surface-micromachined apparatus, comprising:
(a) a microchannel formed on a substrate from a plurality of deposited and patterned layers of polycrystalline silicon and silicon nitride, with the silicon nitride at least partially lining the microchannel and with the microchannel further including a plurality of spaced posts extending outward from at least one wall thereof, with the posts being lined with silicon nitride; and
(b) means for generating an electroosmotic force or electromagnetic field in the microchannel.

31. A surface-micromachined apparatus, comprising:
(a) a microfluidic channel formed on a substrate and defined, at least in part, by a first layer of silicon nitride, and a second layer of silicon nitride overlying the first layer, with the second silicon nitride layer being nonplanar and thereby forming a constricted portion of the channel having a height that is smaller than the height of the remainder of the channel; and
(b) means, located within the channel, for generating a flow of a fluid in the channel.

32. The apparatus of claim 31 wherein the substrate comprises silicon.

33. The apparatus of claim 31 wherein the channel is further defined by at least one layer of polycrystalline silicon overlying the second layer of silicon nitride.

34. The apparatus of claim 33 wherein a pair of layers of the polycrystalline silicon overlying the second layer of silicon nitride are separated by a third layer of silicon nitride.

35. The apparatus of claim 31 wherein the flow generating means comprises a first plurality of electrodes disposed in the channel, with the first plurality of electrodes being spaced about the length of the channel to generate an electroosmotic force on the fluid in response to a voltage applied between at least two of the first plurality of electrodes.

36. The apparatus of claim 35 further including a second plurality of electrodes disposed in the channel or proximate thereto, with the second plurality of electrodes being spaced across a lateral dimension of the channel to alter the flow of the fluid in the channel.

37. The apparatus of claim 36 wherein the first plurality of electrodes are substantially planar and are oriented in a direction substantially perpendicular to the substrate.

38. The apparatus of claim 37 wherein the second plurality of electrodes are substantially planar and are oriented in a direction substantially perpendicular to the substrate.

39. The apparatus of claim 37 wherein the second plurality of electrodes are substantially planar and are oriented in a direction substantially coplanar with the substrate.

40. The apparatus of claim 35 further including electrical wiring formed on the substrate below the first layer of silicon nitride or above the second layer of silicon nitride and connected to the first plurality of electrodes to provide the voltage thereto.

41. The apparatus of claim 31 wherein the channel includes an entrance port on one side of the constricted portion, and an exit port on the other side of the constricted portion.

42. The apparatus of claim 41 wherein at least one of the entrance port and the exit port extend through the thickness of the substrate.

43. The apparatus of claim 31 wherein the flow generating means comprises a coil formed about the channel to produce an electromagnetic field in response to an electrical current flowing through the coil.

44. The apparatus of claim 43 wherein the coil is formed from a plurality of turns of an electrical conductor, with each turn further comprising a first portion of the electrical conductor underlying the first layer of silicon nitride, and a second portion of the electrical conductor overlying the second layer of silicon nitride.

45. The apparatus of claim 43 further including electrical wiring formed on the substrate below the first layer of silicon nitride or above the second layer of silicon nitride, with the electrical wiring being connected to the coil to provide the electrical current thereto.

46. The apparatus of claim 31 further including a closed chamber having a deformable or moveable wall in communication with one end of the channel, with the wall being deformable or moveable in response to a change the flow of the fluid in the channel.

47. The apparatus of claim 46 further including means, operatively connected to the deformable or moveable wall of the chamber, for transmitting a displacement of the wall to a load.

48. The apparatus of claim 47 wherein the displacement transmitting means is selected from the group comprises an actuator arm, a lever, a linkage, a compliant mechanism or a combination thereof.

49. A surface-micromachined apparatus, comprising:
(a) a fluid-flow channel formed on a silicon substrate and lined, at least in part, with silicon nitride;
(b) a plurality of vertically-disposed electrical conductors spaced along a portion of the length of the channel, with the vertically-disposed electrical conductors being oriented substantially perpendicular to the substrate; and
(c) electrical wiring connected to the vertically-disposed electrical conductors for electrical activation thereof.

50. The apparatus of claim 49 wherein the vertically-disposed electrical conductors are located proximate to the channel and produce upon electrical activation an electroosmotic force on a fluid within the channel, thereby moving or pressurizing the fluid.

51. The apparatus of claim 50 wherein a portion of the channel is constricted with a lateral dimension smaller than the lateral dimension of the remainder of the channel.

52. The apparatus of claim 50 further including a plurality of horizontally-disposed electrical conductors oriented substantially parallel to the substrate, with each horizontally-disposed electrical conductor being electrically connected to a pair of the vertically-disposed electrical conductors, thereby forming a coil about the channel.

53. The apparatus of claim 52 wherein the coil upon electrical activation produces an electromagnetic field which acts upon a fluid within the channel, thereby moving or pressurizing the fluid.

* * * * *